United States Patent
Dill

(10) Patent No.: US 10,019,688 B2
(45) Date of Patent: *Jul. 10, 2018

(54) SYSTEM AND METHODS FOR THE SELECTION, MONITORING AND COMPENSATION OF MENTORS FOR AT-RISK PEOPLE

(71) Applicant: David A. Dill, Newtown, PA (US)

(72) Inventor: David A. Dill, Newtown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/337,799

(22) Filed: Oct. 28, 2016

(65) Prior Publication Data

US 2018/0075377 A1 Mar. 15, 2018

Related U.S. Application Data

(63) Continuation of application No. 15/266,384, filed on Sep. 15, 2016.

(51) Int. Cl.
*G06Q 10/06* (2012.01)
*G06Q 30/02* (2012.01)

(52) U.S. Cl.
CPC ..... *G06Q 10/0635* (2013.01); *G06Q 30/0208* (2013.01)

(58) Field of Classification Search
None
See application file for complete search history.

(56) References Cited

U.S. PATENT DOCUMENTS

| | | | |
|---|---|---|---|
| 6,470,316 B1* | 10/2002 | Chihara | G10L 13/033 704/260 |
| 8,472,862 B2 | 6/2013 | Yaskin et al. | |
| 9,416,420 B2* | 8/2016 | Faham | C12Q 1/6883 |
| 2003/0037063 A1* | 2/2003 | Schwartz | G06Q 40/08 |
| 2003/0088434 A1* | 5/2003 | Blechman | G06Q 10/10 705/2 |
| 2003/0233278 A1* | 12/2003 | Marshall | G06Q 30/00 705/14.35 |
| 2006/0155558 A1 | 7/2006 | Corpening | |
| 2007/0094039 A1* | 4/2007 | Grant | G06Q 10/00 705/1.1 |
| 2007/0122780 A1 | 5/2007 | Moon et al. | |
| 2008/0071578 A1* | 3/2008 | Herz | G06Q 10/0635 705/3 |
| 2012/0117188 A1 | 5/2012 | Nidiffer et al. | |

(Continued)

OTHER PUBLICATIONS

International Search Report and the Written Opinion of the International Searching Authority of Application No. PCT/US2017/049418 dated Nov. 13, 2007.

(Continued)

*Primary Examiner* — Thomas L Mansfield
(74) *Attorney, Agent, or Firm* — Ping Wang; Morris, Manning & Martin, LLP

(57) ABSTRACT

A method for providing incentive to mentors of at-risk mentees is described. The method comprises the steps of determining an at-risk mentee's behavior and progress in a period of time, determining the mentee's income and income tax payments during the same period of time, and calculating a financial incentive to the mentee's mentor, wherein the amount of the financial incentive is calculated based on the mentee's behavior and/or income tax payment during the period of time.

16 Claims, 3 Drawing Sheets

(56) References Cited

U.S. PATENT DOCUMENTS

| | | | |
|---|---|---|---|
| 2012/0221485 A1* | 8/2012 | Leidner | G06Q 10/0635 |
| | | | 705/36 R |
| 2012/0221486 A1* | 8/2012 | Leidner | G06Q 10/0635 |
| | | | 705/36 R |
| 2012/0282576 A1 | 11/2012 | Chenoweth et al. | |
| 2013/0318005 A1 | 11/2013 | Bass et al. | |
| 2014/0032291 A1 | 1/2014 | Sheperd | |
| 2014/0278730 A1* | 9/2014 | Muhart | G06Q 10/0635 |
| | | | 705/7.28 |
| 2015/0324467 A1 | 11/2015 | Belton, Jr. et al. | |
| 2016/0092906 A1 | 3/2016 | Cioffi | |
| 2016/0098530 A1 | 4/2016 | Dill et al. | |

OTHER PUBLICATIONS

File History of U.S. Appl. No. 15/266,384, filed Sep. 15, 2016.

* cited by examiner

SYSTEM AND METHODS FOR THE SELECTION, MONITORING AND COMPENSATION OF MENTORS FOR AT-RISK PEOPLE

This application is a Continuation of U.S. application Ser. No. 15/266,384, filed on Sep. 15, 2016. The entirety of the aforementioned application is incorporated herein by reference.

FIELD

This disclosure is generally related to systems and methods for mentoring at-risk people. In particular, this disclosure is related to systems and methods for improving matching between mentors and mentees, improving the success of relationships between mentors and mentees, and for providing incentives to mentors.

BACKGROUND

Current mentoring systems operate on a very small scale for a short period of time. Even though current mentoring systems operate on a very small scale for a short period of time, the mentoring systems still provide a substantial impact on, for example, children from troubled backgrounds and people who have recently been released from prison. However, in the current mentoring systems, no quantitative method exists for pairing a potential mentee with a potential mentor with a view to maximizing a probability of a successful mentor-mentee relationship on a long term basis. Additionally, in current mentorship systems, the mentor is not financially compensated for being a successful mentor and has little incentive to establish a long term supportive relationship with the mentee.

Accordingly, there is a need for systems and methods for improving the pairing between mentors and mentees. There is also a need for systems and methods for financially compensating successful mentors on a long term basis.

SUMMARY

One aspect of the present application relates to a method for providing mentoring service to at-risk people. The method comprises the steps of: receiving, via a user interface of an application executing on one or more computer processors, a risk profile concerning an at-risk subject, wherein the risk profile comprises a plurality of risk factors; assigning, via one or more computer processors, a risk point value to each of the plurality of risk factors based on severity level of the subject's risk factors and a risk point matrix stored on a memory device accessible by the one or more computer processors, wherein the risk point matrix is determined by evaluating a large scale data base reflecting risks of other subjects compared to their later successes or failures based on various relevant metrics; determining, via the application, a total risk point value of the subject via the one or more computer processors; and when the total risk point value equals to or exceeds a predetermined threshold value, accepting the at-risk subject as a mentee candidate. Examples of the risk factors include, but are not limited to, age, gender, weight, height, job history, history of traffic violations, alcohol consumption, drug use history, personal medical history, academic performance in school, attendance history at school, extra-curricular activities, gang involvement, personality assessment, probability of dropping out of school, probability of becoming pregnant, probability of gang involvement, probability of committing a crime, probability of using illegal drugs, probability of becoming habitually unemployed, and probability of returning to prison.

In some embodiments, the method further comprises the steps of: assigning, via the one or more computer processors, a mentor candidate to the at-risk subject, wherein the mentor is selected from a mentor qualification database on a memory device accessible by the one or more computer processors; and approving the assigned mentor by an oversight board.

In some embodiments, the method further comprises the steps of: retrieving, via the one or more computer processors, information about how to reduce risks associated with one or more of the plurality of risk factors from a database stored on a memory device, and electronically delivering, via the one or more computer processors, the information to the oversight board and/or a mentor approved by the oversight board.

In some embodiments, the method further comprises the steps of: receiving, via a user interface of the application, the at-risk subject's progress report after the establishment of a mentor-mentee relationship; comparing, via one or more computer processors, the at-risk subject's progress to at-risk children success odds or ex-convict success odds stored on a memory device accessible by the one or more computer processors; providing, via the one or more computer processors, a financial incentive to the mentor based on result of the comparing step; and maintaining, via the one or more computer processors, a mentor incentive database, wherein the mentor incentive database is stored on a tangible medium accessible by the one or more computer processors. In some embodiments, the financial incentive is provided in the form of (1) an income tax credit or a cash payment to the mentor, wherein the amount of the financial incentive is calculated based on the at-risk subject's behavior and/or the at-risk subject's income tax payment.

Another aspect of the present application relates to a system for providing mentoring service to at-risk people. The system comprises one or more computer processors; and one or more tangible computer readable media accessible by the one or more computer processors, wherein the one or more tangible computer readable media comprise instructions that, when executed by the one or more processors, causing the one or more processors to perform the following functions: receiving, via a user interface of an application executing on a computer processor, a risk profile concerning an at-risk subject, wherein the risk profile comprises a plurality of risk factors; assigning a risk point value to each of the plurality of risk factors based on severity level of the subject's risk factors and a risk point matrix stored on one or more tangible computer readable media accessible by the one or more computer processors; determining a total risk point value of the subject; and when the total risk point value equals to or exceeds a predetermined threshold value, accepting the at-risk subject as a mentee candidate. In some embodiments, the risk point matrix has been determined by evaluating a large scale data base reflecting risks of other subjects compared to their later successes or failures based on various relevant metrics.

In some embodiments, the one or more tangible computer readable media further comprise instructions that, when executed by the one or more processors, causes the one or more processors to perform one or more of the following steps: assigning a mentor candidate to the at-risk subject, wherein the mentor candidate is selected from a mentor qualification database on a tangible memory device accessible by the one or more computer processor; retrieving, via the one or more computer processors, information about how to reduce risks associated with one or more of the plurality of risk factors from a database stored on the one or more tangible memory device; electronically delivering, via the computer processors, the information to the oversight board and/or a mentor approved by the oversight board; receiving, via a user interface of the application, the at-risk subject's progress report after the establishment of a mentor-mentee relationship; comparing, via the one or more processors, the at-risk subject's progress to at-risk children success odds or ex-convict success odds stored on a memory device accessible by the one or more computer processors; providing, via the one or more processors, a financial incentive to the mentor based on result of the comparing step; and maintaining, via the one or more processors, a mentor incentive database, wherein the mentor incentive database is stored on a tangible memory device accessible by the one or more processor.

Another aspect of the present application relates to a tangible computer readable medium. The tangible computer readable medium comprises instructions stored thereon for providing mentoring service to at-risk people, the instructions when executed by a processor causing the processor to perform the steps of: receiving, via a user interface of an application executing on the computer processor, a risk profile concerning an at-risk subject, wherein the risk profile comprises a plurality of risk factors; assigning a risk point value to each of the plurality of risk factors based on severity level of the subject's risk factors and a risk point matrix stored on one or more tangible computer readable media accessible by the processor; determining a total risk point value of the subject; and when the total risk point value equals to or exceeds a predetermined threshold value, accepting the at-risk subject as a mentee candidate.

In some embodiments, the tangible computer readable medium further comprises instructions when executed by a processor causing the processor to perform the steps of: assigning a mentor candidate to the at-risk subject, wherein the mentor candidate is selected from a mentor qualification database on a tangible memory device accessible by the processor; retrieving, via the one or more computer processors, information about how to reduce risks associated with one or more of the plurality of risk factors from a database stored on the one or more tangible memory device; and electronically delivering, via the computer processors, the information to the oversight board and/or a mentor approved by the oversight board.

In some embodiments, the tangible computer readable medium further comprises instructions that when executed by a processor causes the processor to perform the steps of: receiving, via a user interface of the application, the at-risk subject's progress report after the establishment of a mentor-mentee relationship; comparing, via the one or more processors, the at-risk subject's progress to at-risk children success odds or ex-convict success odds stored on a memory device accessible by the one or more computer processors; providing, via the one or more processors, a financial incentive to the mentor based on result of the comparing step; and maintaining, via the one or more processors, a mentor incentive database, wherein the mentor incentive database is stored on a tangible memory device accessible by the one or more processors.

Another aspect of the present application relates to a computer system for providing incentive to mentors of at-risk mentees. The computer system comprises a computer processor and one or more tangible computer readable media accessible by the computer processor, wherein the one or more tangible computer readable media comprise instructions that, when executed by the one or more processors, causes the one or more processors to perform the steps of: determining a mentee's behavior and progress in a period of time; determining the mentee's income and income tax payments during the same period of time; and calculating a financial incentive to the mentee's mentor, wherein the amount of the financial incentive is calculated based on the mentee's behavior and/or income tax payment during the period of time using a compensation matrix stored in the one or more tangible computer readable media.

BRIEF DESCRIPTION OF THE DRAWINGS

The present invention can be better understood by reference to the following drawings, wherein like references numerals represent like elements. The drawings are merely exemplary to illustrate certain features that may be used singularly or in any combination with other features and the present invention should not be limited to the embodiments shown.

DETAILED DESCRIPTION

Figure 1:
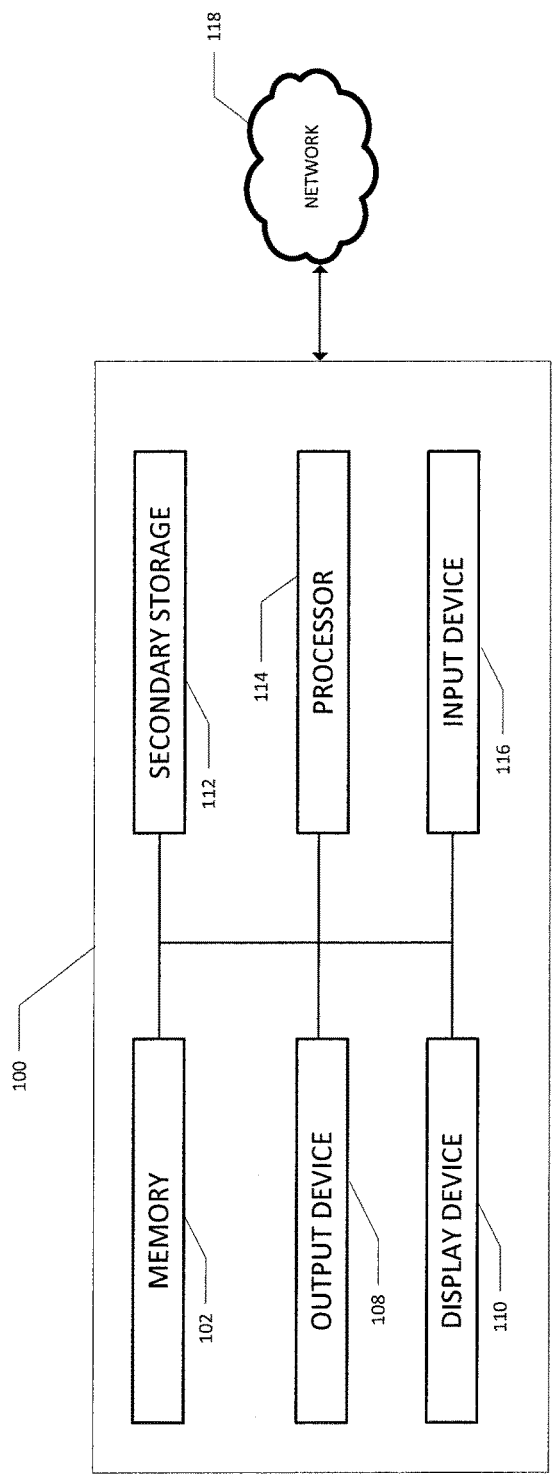
FIG. 1 shows an embodiment of the system of present application

The following detailed description is presented to enable any person skilled in the art to make and use the object of this application. For purposes of explanation, specific nomenclature is set forth to provide a thorough understanding of the present application. However, it will be apparent to one skilled in the art that these specific details are not required to practice the subject of this application. Descriptions of specific applications are provided only as representative examples. The present application is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness.

As used herein, the term "at-risk" refers to individuals, groups, populations or sub-populations who are considered to have a higher probability of failing socially, economically, academically or morally. The term may be applied to those who face circumstances that could jeopardize their ability to complete school, get or retain employment, or avoid criminal activity; such as homelessness, incarceration, teenage pregnancy, serious health issues, domestic violence, transiency, gang activity, drug use, or other criminal activity or conditions, or it may refer to learning disabilities, low test scores, disciplinary problems, grade retentions, or other learning-related factors that have adverse effects.

As used herein, "recidivism" refers to repeated or habitual relapse into a behavior such as crime, or the chronic tendency toward repetition of criminal or antisocial behavior patterns.

As used herein, the term "mentee" refers to an at-risk individual who agrees to accept the instruction, guidance, support and encouragement of an individual tasked with aiding the mentee become a successful member of society.

As used herein, the term "mentor" refers to an individual who provides instruction, guidance, support and encouragement to a mentee for the purpose of aiding the mentee become a successful member of society.

One basic premise that lies behind the present disclosure is that "Success breeds success." Individuals who have exposure to, and guidance from, persons who are successful have a greater chance of becoming successful themselves. Individuals who lack successful role models in their lives experience a greater likelihood of failure or recidivism. Accordingly, the present application seeks to link at-risk children and adults with mentors who will have a lifelong economic motivation to ensure their success. The mentors would be compensated based on the future success of their mentees, such as with some fraction of the income tax payments by their mentees or some other metric reflective of their success as productive citizens. In this manner, the mentors will have a strong ongoing multi-year motivation to advise, coach, implore, train, and otherwise influence the success of their mentees. They would want them to get educated, avoid crime and drug use, and would even be motivated to help them get good jobs. They would be interested in maximizing their long term success. They may share their wisdom, or offer them jobs, or recommend them for certain positions or opportunities. The same principles can be applied to prisoners who have served their time. For such mentors, the economic incentive could be based on income tax payments by their mentees over some extended number of years or it could also include a bonus for each day or week or month or year of crime free activity by their mentees.

Based on the success of various social and charity programs that lack any type of long term economic incentive, applicant has come to the conclusion that a properly constructed large scale effort could radically improve the success rate of at-risk people of all ages, while improving race relations and reducing crime, welfare expenses, and the national debt.

One aspect of the present application relates to a method for providing mentoring service to at-risk people. The method comprises the steps of: receiving, via a user interface of an application executing on one or more computer processors, a risk profile concerning an at-risk subject, wherein the risk profile comprises a plurality of risk factors; assigning, via one or more computer processors, a risk point value to each of the plurality of risk factors based on severity level of the subject's risk factors and a risk point matrix stored on a memory device accessible by the one or more computer processors; determining, via the application, a total risk point value of the subject via the one or more computer processors; and when the total risk point value equals to or exceeds a predetermined threshold value, accepting the at-risk subject as a mentee candidate. Examples of the risk factors include, but are not limited to, age, gender, weight, height, job history, history of traffic violations, alcohol consumption, drug use history, personal medical history, academic performance in school, attendance history at school, extra-curricular activities, gang involvement, personality assessment, probability of dropping out of school, probability of becoming pregnant, probability of gang involvement, probability of committing a crime, probability of using illegal drugs, probability of becoming habitually unemployed, and probability of returning to prison.

In some embodiments, the method further comprises the steps of: assigning, via the one or more computer processors, a mentor candidate to the at-risk subject, wherein the mentor is selected from a mentor qualification database on a memory device accessible by the one or more computer processors; and approving the assigned mentor by an oversight board.

In some embodiments, the method further comprises the steps of: retrieving, via the one or more computer processors, information about how to reduce risks associated with one or more of the plurality of risk factors from a database stored on a memory device, and electronically delivering, via the one or more computer processors, the information to the oversight board and/or a mentor approved by the oversight board.

In some embodiments, the method further comprises the steps of: receiving, via a user interface of the application, the at-risk subject's progress report after the establishment of a mentor-mentee relationship; comparing, via one or more computer processors, the at-risk subject's progress to at-risk children success odds or ex-convict success odds stored on a memory device accessible by the one or more computer processors; providing, via the one or more computer processors, a financial incentive to the mentor based on result of the comparing step; and maintaining, via the one or more computer processors, a mentor incentive database, wherein the mentor incentive database is stored on a tangible medium accessible by the one or more computer processors. In some embodiments, the financial incentive calculation is subject to review by an oversight board so that, if necessary, adjustments can be made for mentees who do not attract appropriate mentors on a timely basis. The oversight board review ensures that all relevant factors are considered to balance supply and demand at a particular point in time within a specific geography for mentors and mentees.

In some embodiments, the financial incentive is provided in the form of (1) an income tax credit or a cash payment to the mentor, wherein the amount of the financial incentive is calculated based on the at-risk subject's behavior and/or the at-risk subject's income tax payment.

The cash payment or share of the at-risk subject's income tax payment to be provided to the mentor may reflect the initial estimates of the risk level faced by the mentee as determined by comparing the mentee's risk factors to those of the historical data base accumulated in the computer system and assessing the likely future performance of the mentee based on those relative risk comparisons. The potential costs of crime, prison, welfare, and other bad events for some people with those risk factors will need to be balanced against the positive impact of those who succeed despite the risk factors. Depending on how severe the risk factors may be, the share of the future income tax payments could be very high while still providing a long term benefit for society if the mentor is successful.

Another aspect of the present application relates to a system for providing mentoring service to at-risk people. The system comprises one or more computer processors; and one or more tangible computer readable media accessible by the one or more computer processors, wherein the one or more tangible computer readable media comprise instructions that, when executed by the one or more processors, cause the one or more processors to perform the following functions: receiving, via a user interface of an application executing on a computer processor, a risk profile concerning an at-risk subject, wherein the risk profile comprises a plurality of risk factors; assigning a risk point value to each of the plurality of risk factors based on severity level of the subject's risk factors and a risk point matrix stored on one or more tangible computer readable media accessible by the one or more computer processors; determining a total risk point value of the subject; and when the total risk point value equals to or exceeds a predetermined threshold value, accepting the at-risk subject as a mentee candidate.

In some embodiments, the one or more tangible computer readable media further comprise instructions that, when executed by the one or more processors, cause the one or more processors to perform one or more of the following steps: assigning a mentor candidate to the at-risk subject, wherein the mentor candidate is selected from a mentor qualification database on a tangible memory device accessible by the one or more computer processor; retrieving, via the one or more computer processors, information about how to reduce risks associated with one or more of the plurality of risk factors from a database stored on the one or more tangible memory device; electronically delivering, via the computer processors, the information to the oversight board and/or a mentor approved by the oversight board; receiving, via a user interface of the application, the at-risk subject's progress report after the establishment of a mentor-mentee relationship; comparing, via the one or more processors, the at-risk subject's progress to at-risk children success odds or ex-convict success odds stored on a memory device accessible by the one or more computer processors; providing, via the one or more processors, a financial incentive to the mentor based on result of the comparing step; and maintaining, via the one or more processors, a mentor incentive database, wherein the mentor incentive database is stored on a tangible memory device accessible by the one or more processor.

Another aspect of the present application relates to a tangible computer readable medium. The tangible computer readable medium comprises instructions stored thereon for providing mentoring service to at-risk people, the instructions when executed by a processor causing the processor to perform the steps of: receiving, via a user interface of an application executing on the computer processor, a risk profile concerning an at-risk subject, wherein the risk profile comprises a plurality of risk factors; assigning a risk point value to each of the plurality of risk factors based on severity level of the subject's risk factors and a risk point stored on one or more tangible computer readable media accessible by the processor; determining a total risk point value of the subject; and when the total risk point value equals to or exceeds a predetermined threshold value, accepting the at-risk subject as a mentee candidate. In some embodiments, the risk point matrix has been determined by evaluating a large scale data base reflecting risks of other subjects compared to their later successes or failures based on various relevant metrics.

In some embodiments, the tangible computer readable medium further comprises instructions when executed by a processor causing the processor to perform the steps of: assigning a mentor candidate to the at-risk subject, wherein the mentor candidate is selected from a mentor qualification database on a tangible memory device accessible by the processor; retrieving, via the one or more computer processors, information about how to reduce risks associated with one or more of the plurality of risk factors from a database stored on the one or more tangible memory device; and electronically delivering, via the computer processors, the information to the oversight board and/or a mentor approved by the oversight board.

In some embodiments, the tangible computer readable medium further comprises instructions when executed by a processor causing the processor to perform the steps of: receiving, via a user interface of the application, the at-risk subject's progress reports after the establishment of a mentor-mentee relationship; comparing, via the one or more processors, the at-risk subject's progress to at-risk children success odds or ex-convict success odds stored on a memory device accessible by the one or more computer processors; providing, via the one or more processors, a financial incentive to the mentor based on result of the comparing step; and maintaining, via the one or more processors, a mentor incentive database, wherein the mentor incentive database is stored on a tangible memory device accessible by the one or more processor.

Another aspect of the present application relates to a computer system for providing incentive to mentors of at-risk mentees. The computer system comprises a computer processor and one or more tangible computer readable media accessible by the computer processor, wherein the one or more tangible computer readable media comprise instructions that, when executed by the one or more processors, cause the one or more processors to perform the steps of: determining a mentee's behavior and progress in a period of time; determining the mentee's income and income tax payments during the same period of time; and calculating a financial incentive to the mentee's mentor, wherein the amount of the financial incentive is calculated based on the mentee's behavior and/or income tax payment during the period of time using a compensation matrix stored in the one or more tangible computer readable media.

In some embodiments, the tangible computer readable medium comprises instructions stored thereon for selecting mentors and/or mentees based on selection factors including in the case of mentors, their relative career and lifetime success, their emotional maturity, their job and family status, their ability and willingness to dedicate the time necessary to be a successful mentor, among other factors, and in the case of mentees, their age, family situation, school performance, school attendance, school dropout rates, gang involvement or temptations, drug use, criminal activity, and maturity, among other factors.

In some embodiments, the tangible computer readable medium comprises instructions when executed by a processor causing the processor to: (1) receive a selection profile concerning a potential mentor or mentee candidate, wherein the selection profile comprises a plurality of selection factors, qualifications of the mentor and/or risks faced by the mentee; (2) assign a selection point value to the potential candidate based on the qualifications of the mentor or the severity level of the potential mentee candidate's risks and the risk point matrix stored in the memory device, wherein better scores are higher scores; (3) assign additional selection point values to the subject based on other selection factors in the potential candidate's selection profile, wherein better scores are higher scores; (4) determine a total selection point value of the potential candidate; and (5a) if the total candidate point value is equal to or exceeds a predetermined threshold value, accept the potential candidate as a mentor or mentee candidate, or (5b) if the total risk point value is below the predetermined threshold, reject the potential candidate as a mentor or mentee candidate. In some embodiments, the rating system in steps (2) and (3) are designed in such a way that better scores are lower scores, including negative scores, and the potential candidate is accepted as a mentor or mentee candidate if the total candidate point value is equal to or below a predetermined threshold value in step (5a), or is rejected as a mentor or mentee candidate if the total candidate point value exceed a predetermined threshold value in step (5b).

In some embodiments, the tangible computer readable medium stores societal costs associated with children who "fail" to become productive. Examples of such costs include, but are not limited to, the costs of prison, welfare, crime, drug use, lack of income tax payments, teenage pregnancy, failing to graduate from high school, and a risk point matrix. In some embodiments, the tangible computer readable medium comprises instructions when executed by a processor causing the processor to: (1) receive a risk profile concerning the mentee subject, wherein the risk profile comprises a plurality of risk factors including the severity level of the subject's probability of dropping out of school or failing in a variety of other ways that will be expensive to society in terms of actual dollars and/or opportunity costs compared to what the mentee might achieve with appropriate guidance; (2) evaluate the expected value of the mentee's life, from society's point of view and compare it to what might be achieved with appropriate guidance; (3) recommend a compensation factor to be assigned to the mentee's mentor that will provide a strong incentive to the mentor while allowing society to retain a significant benefit as well; and (4) recommend a share of the income taxes that will be paid by the mentee and that will then be paid to the mentor by the tax authorities in recognition of mentor's role in ensuring the mentee's success.

In some embodiments, the one or more tangible computer readable media store income and income tax data regarding the mentee and/or the mentee's family in order to: (1) provide a basis for payments to mentors as compensation for their services; (2) provide a periodic basis for analysis of mentee's productivity and success relative to the Success Odds analysis originally projected based on the mentee's risk assessment prior to becoming a mentee; and (3) provide a basis for analysis of mentor's productivity and success relative to the Success Odds analysis originally projected based on the mentee's risk assessment prior to becoming a mentee.

In some embodiments, the tangible computer readable media stores recidivism rates for ex-convicts and compares them to recidivism rates for ex-convicts who become mentees and keeps track of mentor actions designed to help their mentees become successful and keeps track of mentee income and income tax payments in order to: (1) provide a basis for payments to mentors whose mentees avoid future crimes and future prison sentences; (2) provide a basis for determining which mentor actions and strategies are most successful for which types of mentees; (3) provide a basis for determining which mentor qualities and/or qualifications are most helpful for which types of mentees; (4) assign payments to mentors reflecting the time period the mentees have avoided criminal behavior and/or the income tax payments made by the mentees; (5) provide an ongoing database which can be analyzed in order to assign future mentor compensation rates based on the success of the mentoring program; and (6) provide a basis for analyzing the overall costs of recidivism, in terms of court costs, prison costs, and society's costs due to the crimes being committed. The higher amounts of income tax paid by ex-convicts who become mentees may be only a small fraction of the overall benefit to society that is achieved with this program.

FIG. 1 is a block diagram illustrating exemplary hardware components that may be used for implementing aspects of the systems and methods for using incentives to motivate mentoring activities for at-risk people. A computer system 100 may include and execute programs to perform functions described herein, including steps of method described above. While only one processor 114 is shown in FIG. 1, it is understood that the computer system 100 may include multiple processors. Additionally, the system 100 may include multiple networked computers. Further, a mobile device that includes some of the same components of computer system 100 may perform steps of the method described above. Computer system 100 may connect with a network 118, e.g., Internet, or other network, to receive inquires, obtain data, and transmit information (e.g., to a user work station or other user computing device) as described above.

Computer system 100 typically includes a memory 102, a secondary storage device 112, and a processor 114. Computer system 100 may also include a plurality of processors 114 and be configured as a plurality of, e.g., bladed servers, or other known server configurations. Computer system 100 may also include an input device 116, a display device 110, and an output device 108.

Memory 102 may include RAM or similar types of memory, and it may store one or more applications for execution by processor 114. Secondary storage device 112 may include a hard disk drive, floppy disk drive, CD-ROM drive, or other types of non-volatile data storage. Processor 114 may include multiple processors or include one or more multi-core processors. Any type of processor 114 capable of performing the calculations described herein may be used. Processor 114 may execute the application(s) that are stored in memory 102 or secondary storage 112, or received from the Internet or other network 118. The processing by processor 114 may be implemented in software, such as software modules, for execution by computers or other machines. These applications preferably include instructions executable to perform the functions and methods described above and illustrated in the Figures herein. The applications may provide graphic user interfaces (GUIs) through which users may view and interact with the application(s).

Also, as noted, processor 114 may execute one or more software applications in order to provide the functions described in this specification, specifically to execute and perform the steps and functions in the methods described above. Such methods and the processing may be implemented in software, such as software modules, for execution by computers or other machines.

Input device 116 may include any device for entering information into computer system 100, such as a touch-screen, keyboard, mouse, cursor-control device, microphone, digital camera, video recorder or camcorder. Input device 116 may be used to enter information into GUIs during performance of the methods described above. Display device 110 may include any type of device for presenting visual information such as, for example, a computer monitor or flat-screen display (or mobile device screen). Output device 108 may include any type of device for presenting a hard copy of information, such as a printer, and other types of output devices include speakers or any device for providing information in audio form.

Examples of computer system 100 include dedicated server computers, such as bladed servers, personal computers, laptop computers, notebook computers, palm top computers, network computers, mobile devices, or any processor-controlled device capable of executing a web browser or other type of application for interacting with the system. If computer system 100 is a server, server 100 may not include input device 116, display device 110 and output device 108. Rather, server 100 may be connected, e.g., through a network connection to a stand-alone work station (another computer system) that has such devices.

Although only one computer system 100 is shown in detail, the computer system 100 may use multiple computer systems or servers as necessary or desired to support the users, as described above. Aspects may also use back-up or redundant servers to prevent network downtime in the event of a failure of a particular server. In addition, although computer system 100 is depicted with various components, one skilled in the art will appreciate that the server can contain additional or different components. In addition, although aspects of an implementation consistent with the above are described as being stored in memory, one skilled in the art will appreciate that these aspects can also be stored on or read from other types of computer program products or computer-readable media, such as secondary storage devices, including hard disks, floppy disks, or CD-ROM; or other forms of RAM or ROM. Computer-readable media may include instructions for controlling a computer system, such as the computer system 100, to perform a particular method, such as methods described above.

Figure 2:
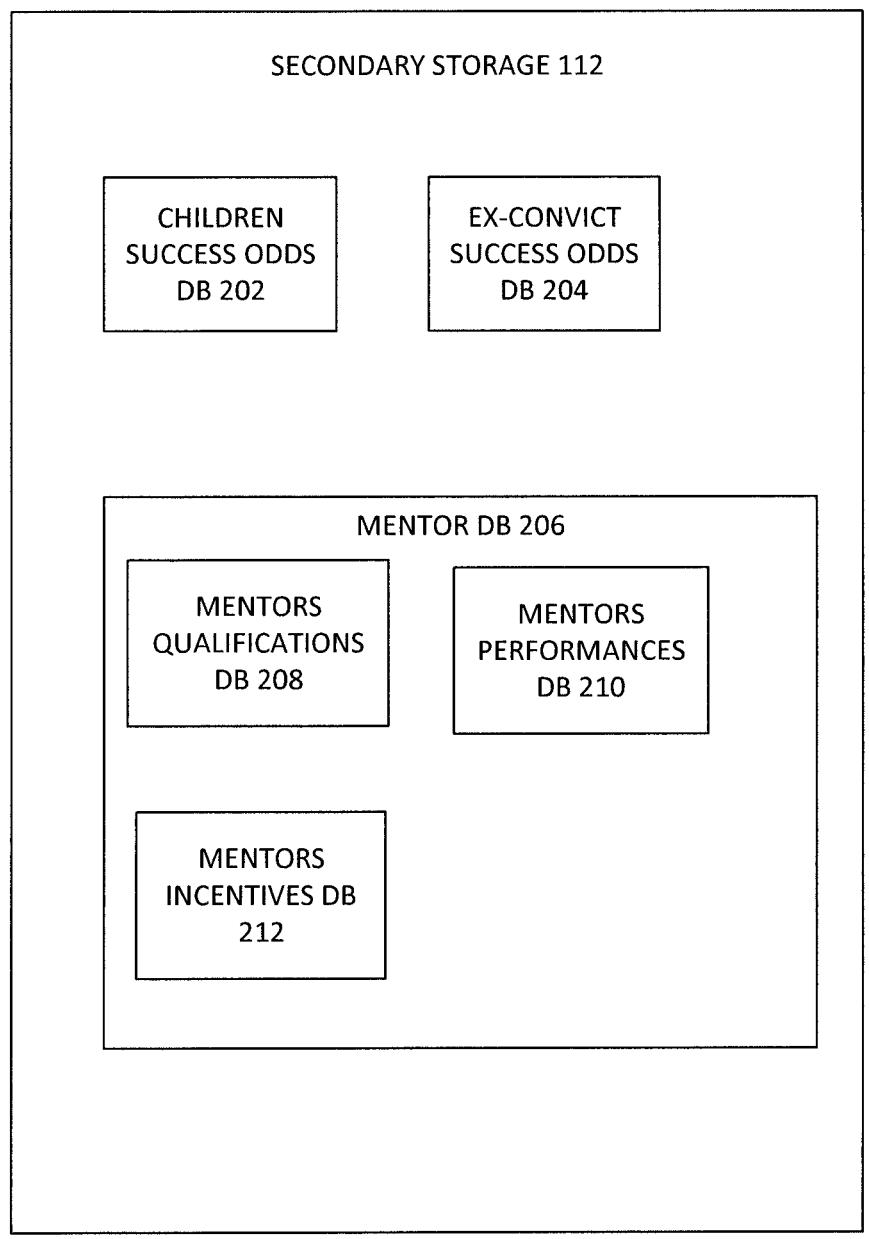
FIG. 2 shows an embodiment of the database structure of the present application.

FIG. 2 shows a plurality of databases (DB) that may be stored in either memory 102, secondary storage 112, or a combination of memory 102 and secondary storage 112. For purposes of description only, this description will assume that the plurality of databases are stored on the secondary storage 112. The plurality of database may include any suitable database, such as a document-oriented database, a full-text database, a spatial database, a distributed database, and a relational database. One of ordinary skill in the art would readily recognize that other types of databases may be used.

Children's Success Odds Database

In one aspect of this disclosure, a first database may be a children success odds DB 202. The children success odds DB 202 may store a plurality of children's records. The children success odds DB 202 may be used to store various attributes or characteristics about each child and his or her life situation stored in DB 202. The various stored attributes or characteristics may comprise a risk profile for each child stored in the children success odds DB 202. For example, the children success odds DB 202 may include attributes or characteristics such as the child's IQ (intelligence quotient), the child's prior success in school (attendance rates, grades, teacher assessments, discipline problems, etc.), the child's family income, the neighborhood or ZIP code of where the child lives, the school the child attends, the dropout rate of the school the child attends, the family status of the child's family, the success of the child's siblings, the child's neighborhood's crime rates, the child's neighborhood's gang activity, and the child's neighborhood's drug use. In some embodiments, the Success Odds (SO) is calculated based on the following formula:

$$SO=f(a,b,c,d,e,f,g,h,I,j)=Aa+Bb+Cc+Dd+Ee+Ff+Gg+Hh++Jj+Kk+Ll$$

wherein a=IQ, b=family income, c=neighborhood assessment, d=school assessment, e=family status, f=sibling success, g=crime rate, h=local drug use, i=dropout rate, j=school success, k=neighborhood gang activity, l=other factors, and wherein the weight of each contributing factor may be modified by a modifying factor (e.g., A, B, C, D, E, F, G, H, I, J, K, or L).

One of ordinary skill in the art would readily recognize that other attributes or characteristics may be stored in the children success odds DB 202. Based on these attributes or characteristics, the system 100 may generate a risk point value for each child using a probability of various life events. For purposes of description only, the remainder of this disclosure will assume that the higher the risk point value, the more likely the child is at-risk. In another aspect of this disclosure the risk point value is defined in such a manner that, the lower the risk point value, the more likely the child is, at-risk. For example, the various life events may include graduating from high school, graduating from college, becoming a contributing member of society, future drug use, future criminal conviction, future unemployment, future welfare assistance, or future premature death. One of ordinary skill in the art would readily recognize that other life events may be calculated using the attributes or characteristics about each child stored in the children success odds DB 202. To generate the risk point value for each child, the system 100 may assign a certain number of points for each of the life events described above. The system 100 may then simply add all of the points to generate the risk point value. Alternatively, the system 100 may assign a weighting factor to each of the life events. The system 100 may then generate the risk point value using weighting factors and the points for each life event described above. Likewise, there may be attributes which correlate in a way that affects the risks for some children. In this case, for example, a child whose siblings all did well may not be affected by gang activity or drug use in the neighborhood; however, if siblings were susceptible to such dangers, then the weight of these risks would be magnified. So the simplistic formula above may become more complicated as analysis of the available data demonstrates interrelationships of risk factor that need to be evaluated by the computer system.

In another aspect of this disclosure, the system 100 may add to the risk point value that was calculated based on the life events described above. For example, the system 100 may factor the sex, the gender, the child's non-academic interests, the section of the country in which the child lives, and the child's overall appearance. One of ordinary skill in the art would readily recognize that other non-life events may be factored in by the system 100. A certain number of risk points may be assigned to these non-life events. These risk points may then be added to the risk points based on life events. Alternatively, these risk points may also be weighted and then added to the risk points based on life events.

Ex-Convict's Success Odds Database

In one aspect of this disclosure, a second database may be an ex-convict success odds DB 204. The ex-convict success odds DB 204 may function similarly to the children success odds DB 202 as described above with the exception that the DB is for ex-convicts rather than children. The ex-convict success odds DB 204 may be used to store various attributes or characteristics about each ex-convict stored in the DB 204. The various stored attributes or characteristics may comprise a risk profile for each ex-convict stored in the ex-convict success odds DB 204. For example, the ex-convict success odds DB 204 may include attributes or characteristics such as the ex-convict's committed crime, the number of years in prison, the ex-convict's education level, the ex-convict's workplace skills, the ex-convict's family support system, the ex-convict's personality, which may be assessed by a trained professional, the ex-convict's drug use history, the ex-convict's gang involvement history, and other factors that may be used by evaluating historical recidivism data. Based on these attributes or characteristics, the system 100 may generate a risk point value for each ex-convict. For purposes of description only, the remainder of this disclosure will assume that the higher the risk point value, the more likely the ex-convict is at-risk. In another aspect of this disclosure the risk point value is defined in such a manner that, the lower the risk point value, the more likely the ex-convict is, at-risk. One of ordinary skill in the art would readily recognize that other attributes or characteristics may be stored in the ex-convict success odds DB 204. To generate the risk point value for each ex-convict, the system 100 may assign a certain number of points for each of the attributes or characteristics described above. The system 100 may then simply add all of the points to generate the risk point value. Alternatively, the system 100 may assign a weighting factor each of the attributes or characteristics. The system 100 may then generate the risk point value using weighting factors and the points for each attribute or characteristic described above.

In some embodiments, the prospects of ex-convicts ($SO_{ExCon}$) are evaluated based on the following formula:

$$(SO_{ExCon})=f(a,b,c,d,e,f,g,h,i)=Aa+Bb+Cc+Dd+Ee+Ff+Gg+Hh+Ii$$

Wherein a=crime committed, b=years in prison, c=education, d=workplace skills, e=family support system, f=personality assessment by a trained professional, g=drug use history, h=gang involvement history, i=other factors found by evaluating historical recidivism data, and wherein the weight of each contributing factor may be modified by a modifying factor (e.g., A, B, C, D, E, F, G, H or I). As with the formula for children, the equation above may need to be significantly more complicated if it is determined that various factors are interrelated in their effects.

If the Success Odds are below a certain level, then clearly intervention by a mentor could be very valuable. As the mentor-mentee relationship continues, data could also be collected regarding the impact of mentors on various "types" of at-risk children, for example the impact of mentoring on children with Success Odds of 20-30% vs. the impact of mentoring on children with Success Odds of 0-10%. In some embodiments, the amount of mentor incentive varies depending on the magnitude of the challenge that the mentor will face in helping his or her mentee to succeed. In some embodiments, mentors are assigned to mentees of the same gender. In some embodiments, mentors are assigned to mentees of different gender. In some embodiments, mentors are assigned to mentees of the same ethnicity. In other embodiments, mentors are assigned to mentees of different ethnicity. Other factors to be considered for mentor/mentee pairing include regularity of interaction, geographic distance, the family situation of the mentor, the job status of the mentor, etc. In some embodiments, the system analyzes periodically the past mentor/mentee pairing data and results and determines what seems to be working and what seems to be failing. The knowledge accumulated in the analysis is used to improve future pairings as well as to advise current mentors and mentees about which behavior characteristic they should consider employing for best results.

The risk of recidivism for ex-convicts can be calculated in a way similar to the Success Odds of young children. In some embodiments, the mentor-mentee relationship is established with an in-prison mentor while an ex-con mentee is in prison and the mentoring continues with an outside mentor after the mentee is released from the prison. In some embodiments, the in-prison mentor is selected from people who work in prison and the outside mentor is selected from people who work outside of prison. In some embodiments, the in-prison mentors are paid based on the recidivism rates of the ex-con mentees and the outside mentors are paid based on the ex-con mentees' income tax payments.

Mentors' Databases

In one aspect of this disclosure, a third database may be the mentors' DB 206. The mentors' DB 206 may be comprised of a plurality database. The mentors' DB may be comprised of, for example, a mentor's qualifications DB 208, a mentor's performances DB 210, and a mentor's incentives DB 212. One of ordinary skill in the art would readily recognize that more or fewer databases may be used.

The mentors' qualifications DB 208 may be used to store a plurality of mentor records. For example, the mentors' qualifications DB 208 may store various attributes or characteristics about each mentor stored in DB 208. For example, the mentors' qualifications DB 206 may include attributes or characteristics such as each mentor's education, profession, criminal history, health history, drug use history, leadership roles or positions, family status, or any other attributes or characteristics that may be helpful in being a successful mentor. A mentor profile may be generated for each mentor using these attributes or characteristics. One of ordinary skill in the art would readily recognize that other attributes or characteristics may be used when generating the mentor profiles. There may also be "free-form" entries, such as leadership positions held within the mentor's community or letters of recommendations or references provided by the mentor attesting to, for example, the mentor's character. The mentors' qualifications may be periodically updated to account for, for example, new references or leadership positions. Longer term, each mentor's track record of success or failure with his or her mentees will also be an important factor in judging the mentor's qualifications in the future.

The mentors' qualifications DB 208 may also store potentially disqualifying attributes or characteristics. For example, if a potential mentor volunteers for the system 100, then the potential mentor may be added to the mentor DB 206. However, if it is later found out that the potential mentor is, for example, an alcoholic, a drug user, a criminal or a child molester, the potential mentor would then be disqualified.

In addition to qualifications, the mentors' qualifications DB 208 may also include suitability measures for a given mentor-mentee pair. For example, before a mentor is assigned to a mentee, the mentee and mentor may audition each other for, for example, compatibility. The mentors' qualifications DB 208 and the mentee' success odds DB 202 may also store the results of such an audition. Moreover, the mentee may reject a mentor after a mentor-mentee relationship has been established. In such a case, the mentors' qualifications DB 208 may include a note indicating that the mentor is not suitable for the mentee. Depending on the contents of that note, the mentor may not be considered suitable for any future mentee. Depending on the timing of that note, the mentor's right to any future payments may be eliminated or adjusted.

The mentors' performances DB 210 may also be used to store a plurality of mentor records. For example, the mentors' performances DB 210 may store records related to how well the mentors are performing. One way to assess how well the mentors are performing is by comparing results of the mentees to the children's success odds or the ex-convicts' success odds. The greater the children or ex-convicts are succeeding compared to the respective success odds, the better the mentors are performing. Another way the system 100 may assess how well the mentors are performing is by including reports from various parties. For example, the mentee's parents, teachers, or other interested parties may provide reports discussing how well the mentor is having an impact on the mentee. One of ordinary skill in the art would readily recognize that other performance metrics may be used to determine the efficacy of the mentor. The performance metrics may be collected periodically. In some embodiments, various alerts are provided by the system if results are significantly positive or negative so that appropriate action can be taken to either duplicate or eliminate the behavior reported.

Additionally, the mentors' performances DB 210 may include a plurality of problem-solution pairs. For example, if a mentor reports that a certain solution worked well for a mentee in a given situation, this may be noted in the mentors' performances DB 210. Alternatively, if a mentor reports that a certain solution did not work well for a mentee in a given situation, this also may be noted in the mentors' performances DB 210. Such problem-solution pairs may be useful for other mentor-mentee relationships.

The system 100 may also include an oversight board to track how well the mentors are performing. The board may use the information in the mentors' performances DB 210 to perform the tracking. In addition to tracking how well the mentors are performing, the board may assign a mentor to a mentee. The assignment may take place based on, for example, mentee success odds, mentor qualifications, and mentor performances. Additionally, the board may limit a number of mentees a mentor may have. For example, if a mentor is new and has not yet proven that he is a good mentor, the board may limit the number of mentees the mentor may have at any given time initially. If the mentor performs well, then the board may increase the number of mentees the mentor may have. In any case, it is likely that the allowable number of mentees should grow for each mentor as the mentor demonstrates success and as mentees perhaps require less hours per week as they mature and succeed with their lives.

In some embodiments, the system 100 may retrieve information about how the qualifications of potential mentors in general and/or their specific qualifications with respect to mentoring a specific mentee candidate or type of mentee candidate, and electronically or otherwise deliver the information to the oversight board which will be responsible for approving the assignment of a mentor to the particular mentee. The system 100 may also electronically or otherwise deliver some aspects of the mentor information to potential mentees or their parents or guardians and obtain a response from the potential mentees about their willingness to work with a particular mentor.

In some embodiments, the system 100 evaluates or provides information to the oversight board to evaluate the probability that the potential mentor will be successful in reducing the various risk factors associated with one or more potential mentees. Factors to be analyzed will include their education, job, criminal history, health, drug use, leadership, or other personality trait track records. Their position in the community and references from respectable people testifying to the qualifications of the mentors could also be important. By tracking mentors' qualifications and personal and professional attributes compared to their performance over time, the data will become available to provide future guidance about which potential mentors would be most effective. Correlating these results with the attributes of their respective mentees could also be productive. The best mentor for person X might be far different than the best mentor for person Y.

In some embodiments, the system 100 electronically tracks mentors' performance in guiding their mentees. These could include statistics about the success of the mentees relative to their initial Success Odds and could include reports from the mentees and/or their parents or teachers or other interested parties. Whether data should be collected weekly or monthly or in some other periodic fashion will also be influenced by an ongoing analysis of the data. Higher frequency early in the relationship will certainly make sense, but the time interval may be extended based on stable positive relationships and progress. Of course, learning both the good and the bad aspects of each relationship can be equally important. In some cases, even the mentors may need mentors if particularly challenging situations arise. Having a large scale database that addresses a wide range of possible problems and solutions will be critical in order to get the best results for each mentee on a timely basis. Having a specific database for each mentee will also be important in order to ensure appropriate progress is being made and in order to alert authorities if mentor or mentee behavior appears to be inappropriate or unsuccessful in any way or evidence suggests that the current mentor/mentee relationship needs to be terminated or modified in some way.

In some embodiments, the system 100 electronically tracks the overall results of the mentoring process. When launched on a massive scale, eventually some number of child molesters or criminals or simply ineffective mentors will find their way into the system. It is important that a database and/or emergency information system be constructed so that any improper behavior can be instantly reported and dealt with effectively. In some embodiments, the contracts signed with mentors include clauses that eliminate their right to future payments if improper behavior occurs. Likewise, mentees will need the right to audition mentors and/or reject them down the road if they are not comfortable that the relationship is productive for them. Keeping a careful database of mentor candidates that includes reports of their success and failures will be critical to ensure that mentees are both protected and given the best odds of future success. The database would need to cover the entire nation or perhaps the world to ensure that "bad apples" identified in one jurisdiction do not later take root in another. Likewise, it will no doubt be true that some mentors will develop spectacular ideas that should be quickly copied across the land. Collecting and sharing the bad and the good stories from this database will be extremely valuable.

The mentors' incentives DB 212 may be used to store a plurality of mentor records. The mentor records stored in the mentors' qualifications DB 208, the mentors' performances DB 210, and the mentors' incentives DB 212 may all be identical. The system 100 may incentivize mentors for their efforts. For example, the mentor may receive a portion of his mentee's tax payments. In this way, the mentor and even the mentor's family and friends may be incentivized to maximize the financial well-being of his mentee. There may be some adjustments to this incentive, however. For example, women generally have lower incomes than men. Accordingly, there may be an adjustment factor to correct for such income inequalities. Alternatively, or additionally, the mentor may be compensated based on the mentee's household tax payments. For example, the mentee could be woman who becomes a successful but non-working mother. The mentor may have had a large part to play in that success. However, since the woman is non-working, she does not generate any taxable income. Therefore, sharing in the tax payments based on household income may be a way to appropriately compensate the mentor.

The system 100 may also provide for additional bonuses. These additional bonuses may be based, for example, on specific goals, such as graduating from high school, achieving a specific grade point average, gaining acceptance at a college, avoiding teen pregnancy, drug use, gang activity, or crime. Such goals may not result in any taxable income. Therefore, one way to compensate the mentor may be a tax deduction. The tax deduction may depend on how well the mentee is doing in regard to the specific goal. This could be, for example, a deduction on their own tax bills upon their mentee reaching a certain age without having succumbed to any of these temptations or for having achieved some of these goals. A database would have to be constructed that tracked the performance of the mentees on these and other key factors.

Additionally, a convict who is about to be released from prison or an ex-convict who has already been released from prison may have multiple mentors, such as two. For example, one mentor may be inside the prison and another mentor may be outside the prison. The two mentors may be compensated differently. For example, the mentor inside the prison may be compensated based on the mentee's recidivism. The mentor outside the prison may be compensated based on the mentee's income tax payments.

The initial database describing the Success Odds and the mentor share of future payments will be very important in focusing the work while properly motivating the mentors. It will, however, be equally important to continue to track both the mentees and the mentors in order to determine the success of the relationship and, if possible, the key elements of the success or lack thereof. Any particular mentor may look good on paper, but only time and the database will be able to determine the true efficacy of his or her activities. Both future mentors and mentees may have an opportunity to learn from the success and failures of their predecessors if they are captured properly in the computer system and analyzed carefully.

Mentee Safety and Program Oversight

It will be crucial to ensure that vigilant oversight of this process is in place. When launched on a massive scale, care must be taken to deal with the fact that child molesters, criminals or simply ineffective mentors may find their way into the system. Accordingly, in some embodiments, a database and/or emergency information system will be constructed so that any improper behavior can be instantly reported and dealt with effectively. The contracts signed with mentors may include clauses that eliminate their right to future payments if improper behavior occurs. Likewise, mentees will need the right to audition mentors and/or reject them down the road if they are not comfortable that the relationship is appropriate or productive for them. Keeping a careful database of mentor candidates that includes reports of their success and failures will be critical to ensure that mentees are both protected and given the best odds of future success. In some embodiments, the database would be a nationwide database to ensure that "bad apples" identified in one jurisdiction do not later take root in another. Likewise, it will no doubt be true that some mentors will develop spectacular ideas that should be quickly copied across the land. Collecting and sharing the bad and the good stories from this database will both be extremely valuable.

In some embodiments, another associated database can track the overall mentor review process. An oversight entity may oversee the mentors' behavior and approve each assignment and review the success of the assignment on an ongoing basis. One can imagine various types of misbehavior that could take place in this sort of bureaucracy, so it will be important to track various metrics to ensure the best possible results while encouraging whistle blowers or contrary points of view that may, upon inspection, have great merit. Having an extensive database that is carefully mined on a regular basis will help to ensure that the process gets the best results. Keeping track of drug use, crime, employment rates, graduation rates, dropout rates, teen pregnancy, and other measures of success and failure will be important in assessing the ongoing qualifications of the various mentors. Perhaps initially any mentor should be limited to just 1 or 2 or a few mentees until he or she can establish his or her credentials through the success of the mentees.

Figure 3:
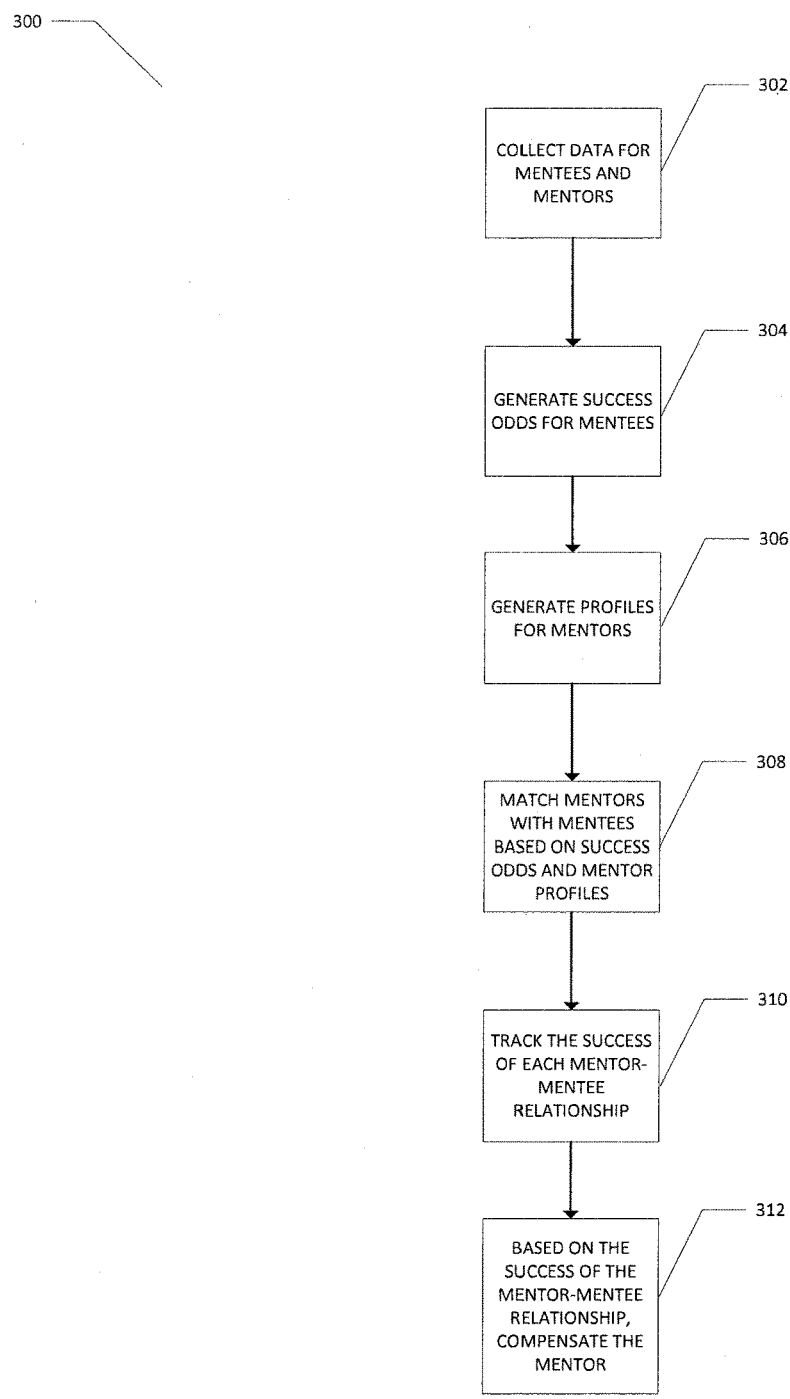
FIG. 3 is a flow chart showing exemplary steps of the method of the present application.

FIG. 3 is a flowchart showing a method 300 to carry out the system 100, according to one aspect of this disclosure. The method 300 may start at block 302. At block 302, the system 100 may collect data for mentees and mentors. The collected data may be used to populate the children success odds DB 202, the ex-convict success odds DB 204, and the mentor DB 206, for example. After block 302 is complete, the method 300 may proceed to block 304.

At block 304, the system 100 may generate success odds for the mentees. The mentees may be, for example, children or ex-convicts. The success odds for the mentees may be calculated as described above in reference to FIG. 2. After block 304 is complete, the method 300 may proceed to block 306.

At block 306, the system 100 may generate profiles for the mentors. The system may generate profiles for the mentors using the information described above in reference to FIG. 2. After block 306 is complete, the method 300 may proceed to block 308.

At block 308, the system 100 may match the mentors with the mentees. The matching may be carried out entirely by the system 100, entirely by the oversight board described above, or by a combination of the system and the oversight board. After block 308 is complete, the method 300 may proceed to block 310.

At block 310, the system 100 may track the success of each mentor-mentee relationship. The system 100 may track the success of the relationships as described above in reference to FIG. 2. After block 310 is complete, the method 300 may proceed to block 312.

At block 312, the system 100 may compensate the mentor based on how successful the mentor-mentee relationship is. The system 100 may gauge the success of the relationships as described above in reference to FIG. 2. After block 312 is complete (which may take years or even decades), the method 300 may end.

In some embodiments, the system 100 will record the key attributes of the mentor and mentee and record the key successes and/or failures along with any relevant data about specific actions that are perceived to have affected this success or failure. In some order to maximize the benefits of this information, it should be constantly evaluated in order to identify patterns and/or creative ideas that show abnormal results, whether they are positive or negative. Any such data perceived to be important should be shared widely on a national or international basis so that mentees, mentors, and oversight boards can get maximum benefits.

The above description is for the purpose of teaching the person of ordinary skill in the art how to practice the object of the present application, and it is not intended to detail all those obvious modifications and variations of it which will become apparent to the skilled worker upon reading the description. It is intended, however, that all such obvious modifications and variations be included within the scope of the present application, which is defined by the following claims. The aspects and embodiments are intended to cover the components and steps in any sequence which is effective to meet the objectives there intended, unless the context specifically indicates the contrary.

What is claimed is:

1. A method for providing mentoring service to at-risk people, comprising the steps of:
   (a) providing a system comprising:
      (i) one or more computing devices in data communication with each other, each device having one or more computer processors, a data communication connection, and one or more tangible non-transitory computer-readable media accessible by the one or more computer processors, and
      (ii) a plurality of databases, including a mentee database, a mentor qualification database, and a mentor incentive database, wherein the mentee database, mentor qualification database and mentor incentive database are each stored in the one or more tangible non-transitory computer-readable media;
   (b) receiving from the mentee database, via a user interface of an application executing on the one or more computer processors, a risk profile concerning an at-risk subject, wherein the risk profile comprises a plurality of risk factors;
   (b) assigning, via the one or more computer processors, a risk point value to each of the plurality of risk factors based on severity level of the subject's risk factors and a risk point matrix stored on a memory device accessible by the one or more computer processors;
   (c) determining, via the one or more computer processors, a total risk point value of the subject via the one or more computer processors;
   (d) accepting the at-risk subject as a mentee when the total risk point value equals to or exceeds a predetermined threshold value;
   (e) assigning, via the one or more computer processors, a mentor to the mentee, thereby establishing a mentor-mentee relationship, wherein the mentor is selected from the mentor qualification database on a memory device accessible by the one or more computer processors;
   (f) receiving, via a user interface of the application, the mentee's progress report after the establishment of the mentor-mentee relationship;
   (g) comparing, via one or more computer processors, the mentee's progress to at-risk population success odds or ex-convict success odds stored on a memory device accessible by the one or more computer processors; and
   (h) calculating, via the one or more computer processors, a financial incentive to the mentor based on step (g); and
   (i) financially compensating the mentor,
   wherein the financial compensation is provided in the form of an income tax credit or a cash payment to the mentor, and
   wherein the amount of the financial compensation is calculated based on the mentee's behavior, progress and/or the mentee's income tax payment(s).

2. The method of claim 1, further comprising the step of: approving the assigned mentor by an oversight board.

3. The method of claim 1, further comprising the step of: retrieving, via the one or more computer processors, information about how to reduce risks associated with one or more of the plurality of risk factors from a database stored on a memory device.

4. The method of claim 3, further comprising the step of: electronically delivering, via the one or more computer processors, the information to an oversight board and/or a mentor approved by the oversight board.

5. The method of claim 1, wherein the plurality of risk factors comprise one or more of the factors selected from the group consisting of age, gender, weight, height, job history, history of traffic violations, alcohol consumption, drug use history, personal medical history, academic performance in school, attendance history at school, extra-curricular activities, gang involvement, personality assessment, probability of dropping out of school, probability of becoming pregnant, probability of committing a crime, probability of using illegal drugs, probability of becoming habitually unemployed, and probability of returning to prison.

6. The method of claim 1, wherein the amount of the financial compensation is based on a share of the at-risk subject's income tax payment, wherein the size of the share is determined by the severity of the mentee's risk factors and potential costs of crime, prison and/or welfare to the society.

7. The method of claim 1, wherein the risk point matrix is determined by evaluating data reflecting risks of other subjects compared to their later successes or failures based on various relevant metrics, as stored in the mentee database.

8. The method of claim 1, wherein the mentee's behavior includes the time period the mentee has avoided criminal behavior.

9. A networked computer system for providing mentoring service to at-risk people, comprising:
   one or more computing devices, each device having one or more computer processors, a data communication connection, and one or more tangible non-transitory computer-readable media accessible by the one or more computer processors, and
   a plurality of databases, including a mentee database, a mentor qualification database, and a mentor incentive database, wherein the mentee database, mentor qualification database and mentor incentive database are each stored in the one or more tangible non-transitory computer-readable media,
   wherein the one or more tangible computer readable media comprise instructions that, when executed by the one or more computer processors, cause the one or more computer processors to perform the steps of:
   (a) receiving from the mentee database, via a user interface of an application executing on the one or more computer processors, a risk profile concerning an at-risk subject, wherein the risk profile comprises a plurality of risk factors;
   (b) assigning, via the one or more computer processors, a risk point value to each of the plurality of risk factors based on severity level of the subject's risk factors and a risk point matrix stored on a memory device accessible by the one or more computer processors,
   (c) determining, via the one or more computer processors, a total risk point value of the subject via the one or more computer processors;
   (d) accepting the at-risk subject as a mentee when the total risk point value equals to or exceeds a predetermined threshold value;
   (e) assigning, via the one or more computer processors, a mentor to the mentee, thereby establishing a mentor-mentee relationship, wherein the mentor is selected from the mentor qualification database on a memory device accessible by the one or more computer processors;

(f) receiving, via a user interface of the application, the mentee's progress report after the establishment of the mentor-mentee relationship;

(g) comparing, via one or more computer processors, the mentee's progress to at-risk population success odds or ex-convict success odds stored on a memory device accessible by the one or more computer processors; and (h) calculating, via the one or more computer processors, a financial incentive to the mentor based on step (g), and (i) financially compensating the mentor, wherein the financial compensation is provided in the form of an income tax credit or a cash payment to the mentor, and wherein the amount of the financial compensation is calculated based on the mentee's behavior, progress and/or the mentee's income tax payment(s).

10. The system of claim 9, wherein the plurality of risk factors comprise one or more of the factors selected from the group consisting of age, gender, weight, height, job history, history of traffic violations, alcohol consumption, drug use history, personal medical history, academic performance in school, attendance history at school, extra-curricular activities, gang involvement, personality assessment, probability of dropping out of school, probability of becoming pregnant, probability of committing a crime, probability of using illegal drugs, probability of becoming habitually unemployed, and probability of returning to prison.

11. The system of claim 9, wherein the assigned mentor is approved by an oversight board.

12. The system of claim 9, wherein the one or more tangible computer readable media further comprise instructions that, when executed by the one or more computer processors, cause the one or more computer processors to retrieve, via the one or more computer processors, information about how to reduce risks associated with one or more of the plurality of risk factors from a database stored on a memory device.

13. The system of claim 12, wherein the one or more tangible computer readable media further comprise instructions that, when executed by the one or more processors, cause the one or more processors to electronically deliver, via the one or more computer processors, the information to an oversight board and/or a mentor approved by the oversight board.

14. The system of claim 9, wherein the risk point matrix is determined by evaluating data reflecting risks of other subjects compared to their later successes or failures based on various relevant metrics, as stored in the mentee database.

15. The system of claim 9, wherein the amount of the financial compensation is based on a share of the mentee's income tax payment, wherein the size of the share is determined by the severity of the mentee's risk factors and potential costs of crime, prison and/or welfare to the society.

16. The system of claim 9, wherein the mentee's behavior includes the time period the mentee has avoided criminal behavior.

* * * * *